United States Patent [19]

Traxler

[11] 4,374,129
[45] Feb. 15, 1983

[54] ANTIBIOTICALLY ACTIVE AMINOPAPULACANDIN DERIVATIVES

[75] Inventor: Peter Traxler, Schönenbuch, Switzerland

[73] Assignee: Ciba-Geigy Corporation, Ardsley, N.Y.

[21] Appl. No.: 330,409

[22] Filed: Dec. 14, 1981

[30] Foreign Application Priority Data

Dec. 16, 1980 [CH] Switzerland .................... 9266/80

[51] Int. Cl.$^3$ .................. A61K 31/71; C07H 13/04
[52] U.S. Cl. ................................. 424/180; 536/16.8
[58] Field of Search ............. 536/17 R; 424/180, 181

[56] References Cited

U.S. PATENT DOCUMENTS

| | | | |
|---|---|---|---|
| 3,956,274 | 5/1976 | Umezawa et al. ............. | 536/17 R |
| 3,960,833 | 6/1976 | Naito et al. ................... | 536/17 R |
| 4,251,517 | 2/1981 | Traxler .......................... | 536/17 R |
| 4,278,665 | 7/1981 | Traxler et al. ................. | 424/181 |

OTHER PUBLICATIONS

P. Traxler et al., Journal of Antibiotic, 33, 967/1980.

*Primary Examiner*—Johnnie R. Brown
*Attorney, Agent, or Firm*—Norbert Gruenfeld; Prabodh I. Almaula

[57] ABSTRACT

N-acylated 11-amino derivatives of papulacandin A or B of the formula I

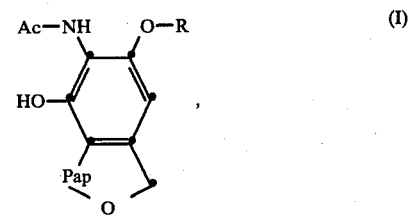

in which Pap is the remainder of papulacandin A or B, R represents methyl or hydrogen and Ac represents the acyl radical of an organic acid, including salts of compounds with salt-forming properties, are distinguished by their antibiotic, especially antimycotic, action and can be used for combating infections of that type, especially those caused by *Candida albicans*. The compounds are produced according to conventional processes from corresponding 11-unsubstituted papulacandin derivatives.

18 Claims, No Drawings

ANTIBIOTICALLY ACTIVE AMINOPAPULACANDIN DERIVATIVES

The present invention relates to antibiotically active aminopapulacandin derivatives, and especially to N-acylated 11-amino derivatives of papulacandin A and B which are of interest owing to their good antibiotic action against fungi and also as intermediates for the manufacture of other antibiotically active papulacandin derivatives.

In the German Offenlegungsschrift 2,609,611 novel antibiotic "A 32283" has been described which is obtained by growing the strain *Papularia sphaerosperma* (Pers.) Höhnel NRRL 8086. As disclosed in that Offenlegungsschrift, this antibiotic, which is today called "papulacandin", consists chiefly of two antibiotically active components, namely approximately 70% of a component B (papulacandin B) and approximately 20% of a component A (papulacandin A), the remainder (approximately 10%) comprising several structurally related secondary components.

The definitive structure of papulacandin A and B has recently been ascertained, cf. P. Traxler, H. Fritz, H. Fuhrer and W. Richter: Journal of Antibiotics, 33(9), 967–978 (1980), and is represented by the following formula P

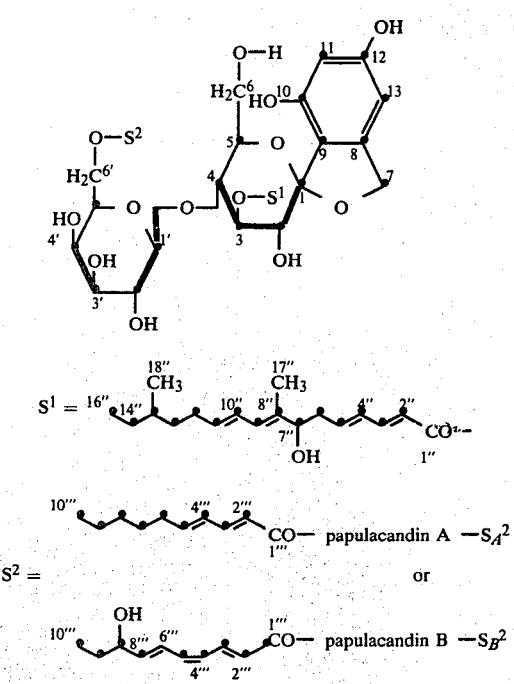

A number of functional derivatives of papulacandin A and B have also been described in the above-mentioned Offenlegungsschrift inter alia ethers in which one or both of the phenolic hydroxy groups are etherified by lower alkanols, especially by methanol.

Like papulacandin A and B, these derivatives have an antimycotic action on thread fungi and on yeast-like fungi, such as, especially, *Candida albicans*.

A particular group of mono- and di-ethers of papulacandin A and B has been described in Belgian Pat. No. 858,492. These compounds, which also have an antibiotic activity against fungi and can, in addition, also be used as intermediates, are characterised by the fact that at least one of the phenolic hydroxy groups is etherified in the 10- and 12-positions by the radical —CH$_2$K, and the symbol K representing, among other meanings, a substituted or unsubstituted carbocyclic hydrocarbon or heterocyclyl radical.

The present invention relates to novel N-acylated 11-amino derivatives of papulacandin A and B of the formula I

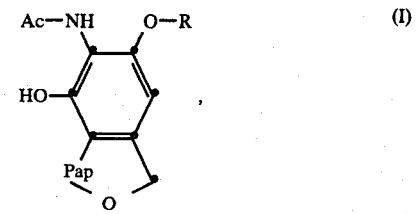

in which Pap represents the remainder of papulacandin A or B, R represents methyl or hydrogen and Ac represents the acyl radical of an organic acid, including salts of compounds having salt-forming properties.

The radical Pap is divalent, both of the free valencies originating from C-1 and having the same steric orientation as in the natural substance of the formula P, and includes both of the sugar rings of papulacandin A or B (C-1 to C-6 and C-1' to C-6') including the acid radicals S$^1$ of the C-18 acid and S$_A^2$ or S$_B^2$ of the C-10 acid characteristic of papulacandin A or B respectively, represented in the formula P; in an analogous manner, the symbols Pap$_A$ and Pap$_B$ relate specifically to the remainder of papulacandin A and B respectively. (Unless expressly mentioned, there is to be understood by the general name papulacandin or Pap, owing to the close relationship between the two, compounds of both of these basic structures or mixtures thereof in any ratio). In general, Pap$_B$ is preferred.

The acyl radical of an organic acid indicated by the symbol Ac is one that is derived from a carboxylic acid, an organic sulphonic acid or a carbonic acid mono-derivative and, preferably, contains a maximum of 18 carbon atoms.

The acyl radical of a carboxylic acid in the meaning of Ac may be one derived from a substituted or unsubstituted acyclic, carbocyclic, carbocyclic-acyclic, heterocyclic or heterocyclic-acyclic carboxylic acid, especially a monocarboxylic acid having a maximum of 18 carbon atoms. The following carboxylic acids may be mentioned by way of example: formic acid, substituted or unsubstituted alkanecarboxylic acids (such as, especially, those given special mention hereinafter), halogenated lower alkane-carboxylic acids (such as chloroacetic acid, bromoacetic acid or α-bromoisovaleric acid), carbocyclic or carbocyclic-acyclic monocarboxylic acids (such as cyclopropane-, cyclobutane-, cyclopentane- and cyclohexanecarboxylic acid, or cyclopropane-, cyclobutane-, cyclopentane- or cyclohexaneacetic acid or -propionic acid), aromatic carbocyclic carboxylic acids (such as benzoic acid), which may be substituted one or more times by halogen atoms (such as fluorine, chlorine or bromine) and/or by hydroxy, lower alkoxy (such as methoxy), lower alkyl (such as methyl) and nitro, aryl- or aryloxy-lower alkanecarboxylic acids and analogues thereof unsaturated in the chain, which may or may not be substituted in the manner indicated above for benzoic acid (such as phenylacetic or phenoxyacetic acid, phenylpropionic acid and cinnamic acid) and heterocyclic acids (such as furan-2- carboxylic acid, 5-tert-butylfuran-2-carboxylic acid, 5-bromofuran-2-carboxylic acid, thiophene-2-carboxylic acid, nicotinic or isonicotinic acid, 4-pyridinepropionic acid, and pyrrole-2- or -3-carboxylic acids that are unsubstituted or substituted by lower alkyl radicals).

An alkanecarboxylic acid forming the basis of the acyl radical Ac preferably has no more than 18 carbon atoms if it is unsubstituted, and preferably no more than 8 carbon atoms if it is substituted. The substituents are firstly hydroxy, mercapto, lower alkylthio (such as methylthio), guanidino, carboxy, esterified carboxy, carboxamido and, especially, primary amino groups, or an imino group bonded at two different carbon atoms, and secondly mono- or bicyclic hydrocarbyl or heterocyclyl radicals, such as, especially, phenyl, p-hydroxyphenyl, 1- or 2-naphthyl, 2-, 3- or 4-pyridyl, 2- or 3-indolyl, 2- or 4-imidazolyl, 2-, 4- or 5-thiazolyl, 2-thienyl or 2-furyl. The acid may carry one or more of the same or different substituents, the total number of carbon atoms, including the carbon-containing substituents, preferably being a maximum of 18. Especially preferred are acyl radicals derived from singly branched or, especially, straight-chain, unsubstituted alkane-(mono or di)-carboxylic acids, the former having a maximum of 18, and the latter having a maximum of 9, carbon atoms, such as, in the first case, acetic, propionic, butyric, isobutyric, valeric, isovaleric, caproic, oenanthic, undecanoic, lauric, myristic, palmitic and stearic acid and, in the second case, malonic, succinic, glutaric, adipic, pimelic and suberic acid.

Especially preferred are acyl radicals derived from amino acids, especially from α-amino acids of the L-series occurring naturally, especially in the form of peptide building units, and closely related analogues thereof such as, especially, the enantiomers of the "unnatural" D-series, which may also be in a protected form, that is to say in such a form in which the amino, hydroxy and/or mercapto groups are substituted by conventional protecting groups customary in peptide chemistry. Among the preferred α-amino acids, there come into consideration, for example, more especially the following: glycine, alanine, valine, leucine, isoleucine, phenylalanine, aspartic acid, glutamic acid, arginine, lysine and histidine, also β-alanine, α-aminobutyric acid, γ-aminobutyric acid, norvaline, isovaline, norleucine and ornithine, as well as, also, asparagine, glutamine, tyrosine, tryptophan, methionine, threonine and serine, and also proline and hydroxyproline, in which the α-amino group is closed by the alkyl radical to form a ring.

The acyl radical of an organic sulphonic acid in the meaning of Ac is especially an acyl radical of an aliphatic or carbocyclic, saturated or unsaturated, aromatic or nonaromatic sulphonic acid, preferably one having a maximum of 12 carbon atoms. Such acids are, inter alia, unsubstituted or substituted, for example halogenated, lower alkanesulphonic acids, cycloalkanesulphonic acids in which the cycloalkyl radical may be mono- or polycyclic, or benzenesulphonic acids optionally substituted by lower alkyl (for example methyl), lower alkoxy (for example methoxy), halogen (for example chlorine or bromine) and/or nitro. There may be mentioned as typical examples of such acids trifluoromethanesulphonic acid, (+)-camphor-10-sulphonic acid, 4-bromobenzenesulphonic acid and 3-nitrobenzenesulphonic acid, and especially ethanesulphonic acid, benzenesulphonic acid, p-toluenesulphonic acid and, more especially, methanesulphonic acid.

The acyl radical of a carbonic acid mono-derivative in the meaning of Ac is especially one derived from a carbonic acid mono-ester or carbonic acid monoamide. The acyl radical that is derived from a carbonic acid mono-ester is preferably a substituted or unsubstituted lower alkoxycarbonyl or aryl-lower alkoxycarbonyl. The former may be substituted, for example by halogen atoms, amino, carboxy and/or esterified carboxy, and the latter may carry at the aryl radical, for example, halogen, lower alkyl, lower alkoxy, amino and/or nitro substituents. The following may be mentioned by way of example: methoxy-, ethoxy-, tert-butoxy-, 2,2,2-trichloroethoxy- and 2-iodoethoxy-carbonyl, and benzyloxy-, 4-nitrobenzyloxy-, 4-bromobenzyloxy-, 4-tolyloxy-, 4-methoxybenzyloxy- and 3,4-methylenedioxybenzyloxy-carbonyl. Such acyl radicals may, however, alternatively be derived from more complicated compounds, such as hydroxycarboxylic acids, for example glycolic or lactic acid, or hydroxyamino acids, such as hydroxyproline, threonine, allothreonine or, especially, serine, of which the hydroxyl group is esterified by carbonyl to form the corresponding carbonic acid mono-ester radical.

An acyl radical based on a carbonic acid monoamide is more closely characterised by the formula

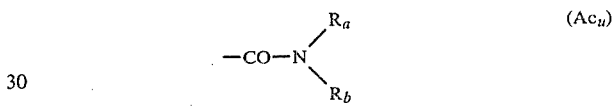

in which each of $R_a$ and $R_b$, independently of one another, represents a hydrogen atom or a substituted or unsubstituted lower alkyl or lower alkanoyl radical having a maximum of 7 carbon atoms, wherein the two radicals $R_a$ and $R_b$ are bonded to one another by a carbon-carbon bond or an oxygen, sulphur or substituted or unsubstituted nitrogen atom and may form together with the nitrogen atom of the amino group a nitrogen-containing heterocyclic ring. The substituents of the lower alkyl and lower alkanoyl radicals are on the one hand hydroxyl, oxo, mercapto (such as methylthio) and amino groups (among the latter preferably primary amino groups and mono- or di-lower alkylamino groups having a maximum total number of 8 carbon atoms, for example methylamino, ethylamino, di-methylamino and diethylamino), and on the other hand monocyclic hydrocarbonyl or heterocyclyl radicals, especially cyclohexyl, phenyl, 4-pyridyl, 2- or 4-imidazolyl, 2-, 4- or 5-thiazolyl, 2-thienyl or 2-furyl. Preferably only one of the radicals $R_a$ and $R_b$ is a lower alkanoyl radical.

A preferred radical $Ac_u$ is, for example, carbamoyl, lower alkylcarbamoyl (such as methylcarbamoyl and ethylcarbamoyl) and di-lower alkylcarbamoyl (such as dimethylcarbamoyl, methylethylcarbamoyl, diethylcarbamoyl, dipropylcarbamoyl or dibutylcarbamoyl), and also lower alkanoylcarbamoyl (such as acetylcarbamoyl or formylcarbamoyl) or lower alkanoyl-lower alkylcarbamoyl (such as N-formyl-N-methylcarbamoyl, N-acetyl-N-methylcarbamoyl, N-formyl-N-ethylcarbamoyl or N-acetyl-N-ethylcarbamoyl). A radical $Ac_u$ in which the radicals $R_a$ and $R_b$ are linked by a C—C bond, preferably a single C—C bond, is, for example, 1-azetidinylcarbonyl, 1-perhydroazepinylcarbonyl, 1-perhydroazocinylcarbonyl and, especially, 1-pyrrolidinylcarbonyl and piperidinocarbonyl, which may also carry the above-mentioned substituents of both kinds or instead substituted, or preferably unsubstituted, lower alkyl radicals, the total number of carbon atoms of such an acyl radical being at most 15. Among such radicals the following may be mentioned by way of example: a 1-pyrrolidinylcarbonyl substituted by hydroxy, carboxy, esterified carboxy or oxo, a piperidinocarbonyl substituted by formyl, carboxy, lower alkoxycarbonyl, carbamoyl or oxo, the substituent preferably being in the 4-position or, when it is oxo, alternatively in the 2-position; a lower alkyl-, 1-hydroxy-lower alkyl- or 2-hydroxy-lower alkyl-piperidinocarbonyl, the radical preferably being in the 4-position, and 1-(2-oxoperhydroazepinyl)-carbonyl.

A radical $Ac_u$ in which the heterocyclic ring is formed by the linking of the radicals $R_a$ and $R_b$ by means of an oxygen or sulphur (II) atom is, for example, morpholinocarbonyl, thiomorpholinocarbonyl or 3-thiazolidinylcarbonyl.

In a radical $Ac_u$ in which the heterocyclic ring is formed by the linking of the radicals $R_a$ and $R_b$ by means of an optionally substituted nitrogen atom, this nitrogen atom is characterised by the partial formula $$>N-R_N$$

in which $R_N$ may represent hydrogen, formyl, carboxy, lower alkoxycarbonyl (such as methoxy- and ethoxycarbonyl), carbamoyl and, especially, an acyclic or monocyclic hydrocarbon having a maximum of 8 carbon atoms, for example lower alkyl (especially methyl), lower alkenyl (such as allyl), lower alkynyl (such as propargyl), phenyl, phenyl-lower alkyl (especially benzyl) and also hydroxy-lower alkyl (especially 2-hydroxyethyl). Such a radical $Ac_u$ is especially a 1-morpholinylcarbonyl, 1-pyrimidinylcarbonyl or 1-imidazolidinylcarbonyl, which may be substituted in the manner indicated above both at its carbon atoms and also at the other nitrogen atom. Of the substituents of the carbon atoms, especially the oxo group shall be mentioned, especially when it is positioned at the carbon atom next to the central nitrogen atom. Especially preferred acyl radicals of this type are characterised by the formula $Ac_t$

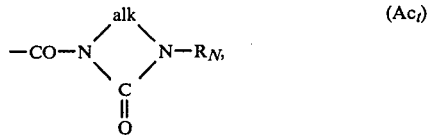

in which $R_N$ has the meaning given above and alk represents an alkylene radical having from 2–8 carbon atoms which separates the two nitrogen atoms from one another by a minimum of 2, and a maximum of 4, carbon atoms. Preferably $R_N$ represents hydrogen, lower alkyl having from 1–4 carbon atoms, especially methyl, or benzyl; the symbol alk preferably represents tetramethylene, trimethylene or, especially, ethylene. Of the acyl radicals of the formula $Ac_t$, especially the following shall be mentioned: 1-(2-oxoperhydro-1,3-diazepinyl)-carbonyl, 1-(2-oxopyrimidinyl)-carbonyl, 1-(3-methyl-2-oxopyrimidinyl)-carbonyl, 1-(3-benzyl-2-oxoimidazolidinyl)-carbonyl, 1-(3-methyl-2-oxoimidazolidinyl)-carbonyl and, more especially, 1-(2-oxoimidazolidinyl)-carbonyl.

Among the compounds of the formula I according to the invention, there are preferred those in which Pap is $Pap_B$, R represents methyl or, preferably, hydrogen, and Ac represents a lower alkanoyl, especially acetyl.

Among the compounds of the formula I according to the invention there are also preferred those in which Pap is $Pap_B$, R represents methyl or, preferably, hydrogen and Ac represents the acyl radical of a naturally occurring α-amino acid, especially glycyl, alanyl, α- or β- aspartyl, asparaginyl, α- or γ-glutamyl or glutaminyl.

Among the compounds of the formula I according to the invention there are especially preferred those in which Pap is $Pap_B$, R represents methyl or, preferably, hydrogen, and Ac represents the acyl radical of a benzenesulphonic or lower alkanesulphonic acid, especially methanesulphonic acid, optionally substituted by halogen, nitro, methoxy or methyl.

Among the compounds of the formula I according to the invention there are more especially preferred those in which Pap is $Pap_B$, R represents methyl or, preferably, hydrogen, and Ac represents the above-defined acyl radical $Ac_t$, especially one such acyl radical in which alk represents ethylene and $R_N$ represents hydrogen, methyl or benzyl.

More especially preferred are compounds of the above formula I in which Ac represents an acyl radical according to the Examples, or which have the basic structure of one of the papulacandin derivatives illustrated in the Examples. There are thus preferred above all the N-acylated papulacandin derivatives illustrated in the Examples.

Those of the compounds of the formula I above characterised generally or as preferred that contain a free carboxy group may alternatively be in the form of salts, for example sodium, potassium, calcium or magnesium salts, or alternatively ammonium salts derived from ammonia or from a nitrogen-containing organic base, which are able to form physiologically tolerable salts with compounds of the formula I. Those of the compounds of the formula I above characterised generally or as preferred that contain a free amino group may alternatively be in the form of salts, namely acid addition salts. There come into consideration as acid addition salts physiologically tolerable salts with customary therapeutically usable acids; of the inorganic acids there may be mentioned hydrohalic acids, such as hydrochloric acid, but also sulphuric acid and phosphoric or pyrophosphoric acid, and of the organic acids especially sulphonic acids, for example benzenesulphonic or p-toluenesulphonic acid, or lower alkanesulphonic acids, such as methanesulphonic acid, as well as carboxylic acids, such as acetic acid, lactic acid, palmitic and stearic acid, malic acid, tartaric acid, ascorbic acid and citric acid. Compounds that contain both an amino group and a free carboxy group may alternatively be in the form of inner salts.

Unless stated otherwise, the names of the amino acids and their abbreviated names relate to α-amino acids of the L-series that occur naturally.

Unless stated otherwise, the term "lower", whenever used in connection with an organic radical or compound, indicates such a radical or compound having a maximum of 7, but preferably a maximum of 4, carbon atoms.

The novel papulacandin compounds according to the invention have an antibiotic action which is fundamentally similar to the action of other papulacandins. They can therefore be used in similar therapeutic indications, for example, especially for combating infections by fungi, especially by *Candida albicans*. They can also be used as valuable intermediates for the manufacture of other therapeutically valuable compounds, for example those having a further modified acyl radical Ac.

The papulacandin derivatives of the formula I according to the invention are obtained using conventional manufacturing processes of preparative organic chemistry that are known per se. They are thus produced, for example, by acylating a corresponding 11-aminopapulacandin derivative with temporary protection of a free hydroxy group present in the 12-position and, if desired, isolating a resulting product having salt-forming properties in the form of a salt. If there are free functional groups, such as hydroxy, carboxy and, especially, amino groups present in the acylating agent which do not participate in the acylation reaction, they can, if necessary, also be temporarily protected and freed after the main reaction. The process according to the invention is especially characterised by reacting an 11-aminopapulacandin derivative of the formula

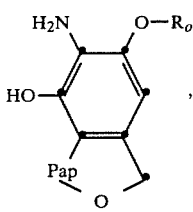  (II)

in which Pap has the meaning given above and $R_o$ represents methyl or a hydroxy-protecting group Y, with an organic acid of the formula AcOH     (III), or a reactive derivative thereof, in which Ac has the meaning given above, where applicable with temporary protection of amino, hydroxy and carboxy groups present in the Ac radicals by appropriate protecting groups X, Y and W respectively, and removing a protecting group Y present in the radical $R_o$ and, if desired, also removing protecting groups present in the radical Ac and, if desired, converting a resulting compound having salt-forming properties into its salt, or a resulting salt into the corresponding free compound.

A reactive derivative of the acid AcOH is, for example, an anhydride, especially a symmetrical anhydride of the formula Ac—O—Ac or a cyclic anhydride of a dicarboxylic acid, such as succinic anhydride or glutaric anhydride, or alternatively a mixed anhydride with another organic acid, for example with trifluoroacetic acid, or especially with an inorganic acid, for example an acid azide or acid halide, especially an acid chloride. A reactive acid derivative is preferably an activated ester, for example one in which the acid AcOH is esterified by 2,4,5-trichlorophenol, pentachlorophenol, pentafluorophenol, 2-nitrophenol or, especially, 4-nitrophenol, or by an N-hydroxy compound, such as N-hydroxysuccinimide, 1-hydroxybenztriazole or N-hydroxypiperidine, or alternatively by an N,N'-disubstituted isourea, such as, especially, N,N'-dicyclohexylisourea, or a similar generally known activating component.

In general, active esters are advantageous as acylating agents because they acylate amino groups preferentially before hydroxy groups and thus make the protection of hydroxy groups superfluous in practice. In the case of dicarboxylic acids, however, cyclic anhydrides are preferred if they are present. To avoid an undesired O-acylation, in general only one equivalent of the acylating agent based on the starting material of the formula II is used.

The acylation is carried out in a manner known per se, preferably in customary solvents, for example dioxan, tetrahydrofuran, acetonitrile, pyridine, dimethylformamide, dimethylacetamide, dimethyl sulphoxide, N-methylpyrrolidone, hexamethylphosphorus triamide, as well as chloroform and methylene chloride, and in expedient mixtures thereof. It is also possible to carry out the reaction with the addition of an organic base, for example a quaternary, or especially tertiary, amine, such as triethylamine, N-ethylmorpholine or N-methylpiperidine, in order to keep the amino group to be acylated in unprotonated form. The reaction temperature is usually from −20° to +50° C., preferably from approximately 0° C. to room temperature. If an excess of acylating agent, such as a symmetrical anhydride, is employed, it is advantageous to use a lower alkanol, especially methanol or ethanol, as solvent, to maintain the reaction temperature between approximately −10° and +25° C. and to halt the reaction once N-acylation is complete (which anyway proceeds substantially more quickly than O-acylation); the suitable moment can be simply ascertained by customary analytical methods, for example by means of thin layer chromatography.

In a special variant of the process, which can chiefly be used with amino acids, the reaction is carried out using an amino acid with an activated terminal carboxy group and a protected α-amino group. The carboxy group can in this case be directly activated in situ by the reaction of a free acid with a carbodiimide, such as N,N'-dicyclohexylcarbodiimide, optionally with the addition of N-hydroxysuccinimide, an unsubstituted or, for example, halogen-, methyl- or methoxy-substituted 1-hydroxybenztriazole or 4-hydroxybenzo-1,2,3-triazine-3-oxide (inter alia cf. DT 2 202 613), or, especially, N-hydroxy-5-norbornene-2,3-dicarboximide, or with N,N'-carbonyldiimidazole. The operating conditions of this and analogous acylation methods are elaborated in great detail in particular as a general method for the synthesis of peptides, cf. Houben-Weyl: Methoden der organischen Chemie; 4th edition, vol. 15/I and II, E. Wünsch (editor): Synthese von Peptiden (Georg Thieme Verlag, Stuttgart; 1974). Especially, the acylation is carried out in the manner illustrated hereinafter by the Examples.

Also the protecting groups X, Y and W used are generally known, especially in peptide chemistry, cf., for example, the above-mentioned reference text. The narrower selection of the protecting groups depends on the specific purpose, it being necessary to take into account in particular the specific properties of the papulacandin radical (ester and ether bonds of the sugar radicals, double bonds of the acyl radicals $S^1$ and $S^2$). In the case of several of the functional groups to be protected, advantageous combinations must be selected. Preferably, for example, similar or, even better, identical protecting groups, are used both in the radical $R_o$ and in the radical Ac and are simultaneously removed following acylation.

There can be used as amino-protecting group X especially amino-protecting groups that can be removed by reduction, for example especially those of the benzyloxycarbonyl type in which the benzyloxycarbonyl group is substituted in the aromatic moiety by halogen atoms, lower alkoxy groups and/or lower alkyl radicals and, especially, by nitro groups, such as the p-chloro- and p-bromobenzyloxycarbonyl, p-methoxybenzyloxycarbonyl, p-tolyloxycarbonyl and, especially, p-nitrobenzyloxycarbonyl group, or alternatively the isonicotinyloxycarbonyl group. An advantageous amino-protecting group X is an ethoxycarbonyl group which carries in the $\beta$-position a silyl group substituted by three hydrocarbon radicals, such as triphenylsilyl, dimethylbutylsilyl or, especially, trimethylsilyl. A $\beta$-(trihydrocarbylsilyl)-ethoxycarbonyl group of this type, such as a $\beta$-(tri-lower alkylsilyl)-ethoxycarbonyl group, for example, especially $\beta$-(trimethylsilyl)-ethoxycarbonyl, forms with the amino group to be protected a corresponding $\beta$-trihydrocarbylsilyl-ethoxycarbonylamino group (for example the $\beta$-trimethylsilylethoxycarbonylamino group), which can be removed only under very specific, very mild conditions by the action of fluoride ions. In this connection it behaves analogously to the $\beta$-silylethyl ester group described hereinafter as a carboxy-protecting group. (This similarity is of particular advantage in the synthesis if in the acyl radical Ac both of these protecting groups are to be removed simultaneously). Further details are given hereinafter in connection with the protection of the carboxy group in the form of a $\beta$-silylethyl ester. Under certain circumstances it is also possible to use groups that can be removed by acidolysis, such as the tert-butoxycarbonyl group and analogous groups as well as, also, those of the aralkyl type, such as benzhydryl, di(4-methoxy)-benzhydryl and triphenylmethyl (trityl), or certain aralkoxycarbonyl groups of the 2-(p-biphenylyl)-2-propoxycarbonyl type, which are described in Swiss Pat. No. 509 266.

There may advantageously be used as hydroxyprotecting groups Y, groups that can be removed by reduction, cf. the above-cited text (Houben-Weyl), and also groups that can be removed by acidolysis, such as 2-tetrahydropyranyl and tert-butyl. Preferred hydroxyprotecting groups that can be removed by reduction area, for example, benzyl groups that are substituted in the aromatic moiety by halogen, lower alkyl, lower alkoxy and/or, especially, nitro, especially the 4-nitrobenzyl group. It is also possible to use acyl groups that can be removed under weakly basic conditions, such as formyl or trifluoroacetyl.

For protection of carboxy groups, these are preferably esterified. The carboxy-protecting groups W customary for this purpose are generally known, cf., for example, the above-cited reference text (Houben-Weyl). There are suitable for the esterification, for example, alcohols that yield radicals that can be removed by acidolysis, such as cyanomethyl alcohol, benzoylmethyl alcohol or tert-butyl alcohol, but especially alcohols that yield radicals which can be removed by reduction, such as 2,2,2-trichloro-ethanol and, especially, 4-nitrobenzyl alcohol, or alternatively isonicotinyl alcohol. An especially advantageous class of substituted alkanols are ethyl alcohols which carry in the $\beta$-position a tri-substituted silyl group, such as triphenylsilyl, dimethylbutylsilyl or, especially, trimethylsilyl. As is described, for example, in Belgian Pat. No. 851.576, these alcohols are particularly suitable for the protection of carboxy groups because the corresponding $\beta$-silylethyl esters, for example $\beta$-(trimethylsilyl)-ethyl ester, have the stability of customary alkyl esters but can selectively be removed under mild conditions by the action of fluoride ions to obtain other esterified carboxy groups, for example in the radical Pap.

The subsequent removal of protecting groups in accordance with the invention depends on their nature and is carried out in each case in a conventional manner known per se taking into consideration the properties of the Pap radical. For this, the removal of a hydroxyprotecting group Y in the radical $R_o$ is a necessary step; on the other hand, a protecting group X, Y and/or W in the Ac radical is removed only if desired. If the protecting groups X, Y and W have been so selected that they can be removed under similar conditions (especially preferred here are the groups removable by reduction that have already been given special mention), then all of these protecting groups are advantageously removed in a single operation; in special cases, however, it is possible to use different types of group and remove each of them individually.

The groups that can be removed by reduction, especially those that contain halogenated lower alkyl radicals (for example 2,2,2-trichloroethyl radicals), isonicotinyl radicals (for example isonicotinyloxycarbonyl) and, especially, substituted benzyl radicals, especially 4-nitrobenzyl radicals of any kind, are preferably removed by zinc reduction, usually in the presence of an acid, preferably acetic acid, and with or without the addition of an inert organic solvent, usually at room temperature. The removal of a protecting group by acid hydrolysis (acidolysis) is carried out in the case of groups of the tert-butyl type by means of hydrogen fluoride or trifluoroacetic acid, and in the case of acid-sensitive protecting groups chiefly by means of a lower aliphaticcarboxylic acid, such as formic acid and/or acetic acid, in the presence of water and, optionally, a polyhalogenated lower alkanol or lower alkanone, such as 1,1,1,3,3,3-hexafluoropropan-2-ol or hexafluoroacetone. In this manner it is possible, for example, for an N-trityl group to be removed by an organic acid, such as formic acid, acetic acid, chloroacetic acid or trifluoroacetic acid, in aqueous or absolute trifluoroethanol as solvent (cf. German Offenlegungsschrift DT No. 2 346 147) or by aqueous acetic acid; for the tert-butoxycarbonyl group to be removed by trifluoroacetic acid or hydrochloric acid; and for the 2-(p-biphenylyl)-isopropoxycarbonyl group to be removed by aqueous acetic acid or, for example, by a mixture of glacial acetic acid, formic acid (82.8% strength) and water (7:1:2) or in accordance with the process in DT No. 2 346 147. The $\beta$-silylethyl ester groups are preferably removed by fluoride-ion-yielding reagents, for example fluorides of quaternary organic bases, such as tetraethylammonium fluoride. Protecting groups that are base-unstable, for example formyl and trifluoroacetyl groups, can be carefully removed by the rapid action of an aqueous sodium or potassium bicarbonate solution or, preferably, aqueous ammonia in an organic solvent, usually at room temperature. The protecting groups are preferably removed under the reaction conditions of the Examples, or under analogous conditions.

Those of the end products according to the invention that contain basic groups are obtained, depending on the manner of isolation, in the form of bases or acid addition salts; analogously, end products having acidic groups may also be in the form of salts. Each form can be converted into the other in known manner. The bases can be obtained from the acid addition salts in a manner known per se. From the bases it is in turn possible to obtain acid addition salts, especially therapeutically usable acid addition salts, by reaction with acids, for example with acids of the type that form the above-mentioned salts. Acids and their salts also stand in a similar relationship to one another. Compounds that have both a free carboxy group and a basic group may be in the form of inner salts and these are obtained, for example, by establishing the isoelectric point.

As a result of the close relationship between the free form and a salt form, hereinbefore and hereinafter there are to be understood by all the free compounds or their salts coming into consideration optionally also the corresponding salts and free compounds, respectively, where appropriate with regard to meaning and purpose.

The invention relates also to those forms of the process in which a compound obtainable as intermediate at any stage of the process is used as starting material and the remaining process steps are carried out, or in which a starting material is formed under the reaction conditions or is used in the form of a derivative, for example a salt, thereof.

In the process of the present invention, the starting materials used are preferably those that lead to the compounds described at the beginning as being especially valuable.

The starting materials of the formula III, that is to say the acids of the formula AcOH and their reactive derivatives, are known or, if they are unknown, can be simply obtained by conventional synthetic processes.

The 11-aminopapulacandin derivatives of the formula II used as starting materials for the process according to the invention

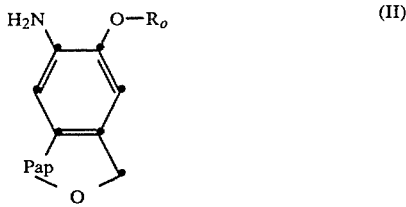 (II)

in which Pap represents the remainder of papulacandin A or B and $R_o$ represents methyl or a hydroxy-protecting group Y, and their acid addition salts, are new and the present invention relates also to these.

The radical Pap is preferably the radical $Pap_B$ of papulacandin B. The hydroxy-protecting group Y is preferably a hydroxy-protecting group that can be removed by reduction, preferably the isonicotinyl group or, especially, the 4-nitrobenzyl group. Preferred as $R_o$, however, is methyl.

Compounds of the formula II, especially those in which $R_o$ represents methyl, are distinguished by antibiotic properties analogous to those of the corresponding acylamino derivatives of the formula I, and can be used for analogous therapeutic purposes.

The compounds of the formula II are manufactured in accordance with the invention by, in succession, (a) reacting a papulacandin derivative of the formula IV

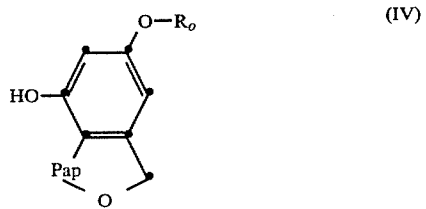 (IV)

in which Pap and $R_o$ have the meanings given above, with an arylselenic acid anhydride and hexa-lower alkyldisilazane and (b) treating with a reducing agent.

The arylselenic acid anhydride is characterised by the formula Ar—(Se=O)—O—(Se=O)—Ar (V), in which Ar is an aryl radical having a maximum of 12 carbon atoms, especially a phenyl radical; the hexa-lower alkyldisilazane has the formula $(Me_3Si)_2NH$ (VI), in which Me represents a lower alkyl radical having from 1–4 carbon atoms, especially methyl. The reaction conditions have already been described in examples of simpler phenols, cf. D. H. R. Barton et al. J. Chem. Soc., Chemical Communications, 1977, 147. In general, the reaction is carried out with a smaller excess of approximately 1.2–1.5 mole equivalent of both reagents (preferably phenylselenic acid anhydride and hexamethyldisilazane), there being used an inert organic solvent, such as an aromatic hydrocarbon (for example benzene or toluene), chlorinated lower alkane (for example methylene chloride or chloroform) or an aliphatic or cyclic ether (for example diethyl ether or 1,2-dimethoxyethane, or tetrahydrofuran or dioxan) at temperatures of from −10° to +30°, preferably 0° to room temperature.

The second stage, that is to say the reduction of the arylselenoimine of the general formula

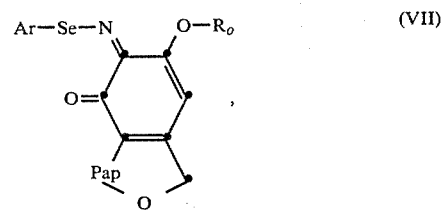 (VII)

obtainable as intermediate, in which Ar, Pap and $R_o$ have the meanings given above, is carried out with the simultaneous removal of the arylseleno group and results in the formation of the 11-amino group and regeneration of the 10-hydroxy group. The reduction is preferably carried out with hydrogen sulphide or an organic substitution derivative thereof, such as an aliphatic or aromatic thiol (for example especially phenylthiol) at a temperature of from approximately −10° to approximately +30°, preferably between 0° and room temperature, and there is used as reaction medium customary inert organic solvents, for example those mentioned for the first stage, especially methylene chloride or chloroform. Preferably, especially when using hydrogen sulphide, the reduction is carried out in the presence of an organic base, especially a tertiary amine, for example triethylamine, N-methylpyrrolidine, N-ethylpiperidine or N,N′-dimethylpiperazine. In general, both of the reactions are carried out in the manner illustrated in the Examples.

The papulacandin-12-derivatives of the above-defined formula IV that can be used as starting materials are known (cf. German Offenlegungsschrift No. 2,609,611 and Belgian Patent No. 858,492) or can be obtained according to processes known from those specifications. The remaining reagents are also known or can be obtained in known manner.

Depending on the method of operation, the compounds of the formula II are obtained in the form of bases or acid addition salts. From the latter the bases can be obtained in a manner known per se. In turn, by reaction with acids corresponding salts, especially therapeutically usable acid addition salts, can be obtained from the bases. Owing to the close relationship between the novel compounds in free form and in the form of their salts, hereinbefore and hereinafter there shall be understood by the free compounds and their salts optionally also the corresponding salts and free compounds, respectively, where appropriate with regard to meaning and purpose.

The compounds according to the invention are distinguished by their valuable pharmacological properties, namely by their antibiotic, especially antimycotic, activity, as may be demonstrated firstly in vitro against various laboratory strains and clinical isolates of *Candida albicans* (in the tested concentration range of 0.1 to 64 μg/ml), and against *Aspergillus fumigatus, Sporotrichum Schenckii, Trichophyton mentagrophytes* and *Microsporum canis* (in the tested concentration range of 1 to 128 μg/ml), and secondly in vivo (mouse) against acute septicaemia by *Candida albicans* (in the tested dosage range of 13 to 90 mg/kg s.c.). Special attention as active ingredients is drawn to 11-amino-12-O-methylpapulacandin B, 11-acetamino-12-O-methylpapulacandin B, 11-mesylamino-papulacandin B, 11-glycylamino-papulacandin B, 12-O-methyl-11-(3-O-L-seryl)-carbonylamino-papulacandin B and, more especially, 11-(2-oxoimidazolidinecarboxamido)-papulacandin B which on subcutaneous administration to mice has a distinct inhibitory action against Candida septicaemia at ED=13 mg/kg.

On the basis of these favourable properties, the invention relates also to the use of the novel papulacandin derivatives according to the invention, alone or in combination with another antibiotic or chemotherapeutic agent, as an agent for combating infections caused by fungi and *Fungi imperfecti*, for example those mentioned, both in the animal or human body, that is to say as a medicine, and outside the human or animal body, for example as a germicide. When used as a medicine, namely both for local and systemic treatment, the active ingredient according to the invention is preferably administered to a warm-blooded animal, especially man, in the form of a pharmaceutical preparation incorporating at least one conventional pharmaceutical carrier or adjunct. The invention relates also to these pharmaceutical preparations.

To produce pharmaceutical preparations, each of the compounds according to the invention, especially one of those given special mention, can be mixed with an inorganic or organic carrier suitable for topical, enteral or parenteral administration. For this there come into consideration such substances that do not react with the novel compound, such as, for example, gelatin, lactose, starch, magnesium stearate, vegetable oils, benzyl alcohol, or other medicament carriers. The pharmaceutical preparations may, for example, be in the form of tablets, dragees, powders, suppositories, or in liquid form as solutions, suspensions, emulsions, creams or ointments. They may or may not be sterilised and/or contain adjuncts, such as preservatives, stabilisers, wetting agents or emulsifiers. They may also contain other therapeutically valuable substances. Also, as is known, the germicides may be mixed with suitable carriers.

The dosage of the active ingredients, for example of the above specially mentioned aminopapulacandin derivatives, is, in principle, analogous to that of recognised antibiotics of the papulacandin type; it depends, however, also firstly on species, body weight, age and individual condition of the warm-blooded animal, and secondly on the mode of administration and, especially, on the particular sensitivity of the causative organism, which can be ascertained in known manner in a routine test for each individual case.

The invention relates also to a method for destroying or inhibiting the growth (i.e. inhibition) of a microorganism sensitive to at least one of the aminopapulacandin derivatives according to the invention, which is characterised by the treatment of that microorganism, or of a medium infected by that microorganism, with an antimicrobially active dose of one of the aminopapulacandin derivatives according to the invention. There is to be understood by "an antimicrobially active dose" that amount of the active ingredient which is sufficient for effective inhibition of the particular microorganism to be treated.

The following Examples illustrate the above-described invention but are in no way intended to limit the scope thereof. Temperatures are quoted in degrees Centigrade. The composition of solvent mixtures is quoted in proportions by volume.

EXAMPLE 1

12-O-(4-Nitrobenzyl)-11-phenylselenoimino-papulacandin B

To a solution of 10 g of 12-O-(4-nitrobenzyl)-papulacandin B in 250 ml of tetrahydrofuran there are added at +5° C., while stirring, 13.7 g of hexamethyldisilizane and, after 5 minutes, 2.7 g of phenylselenic acid anhydride, the solution immediately turning a deep red colour. After 5 minutes, cooling is stopped and the mixture is further stirred for another 15 minutes at room temperature until no starting material can be detected in the thin layer chromatogram. The reaction solution is poured onto ice water and extracted three times with ethyl acetate. The combined organic extracts are washed twice with water, dried over sodium sulphate and concentrated to dryness by evaporation. The evaporation residue is applied to a column of 500 g of silica gel and eluted with mixtures of chloroform with increasing proportions of 2–10% of methanol. By concentration by evaporation of appropriate fractions, 12-O-(4-nitrobenzyl)-11-phenylselenoimino-papulacandin B is obtained in the form of a deep red powder in two portions (3.4 g and 1.9 g).

EXAMPLE 2

11-Amino-12-O-(4-nitrobenzyl)-papulacandin B 3 ml of triethylamine are added to a solution of 2.6 g of 12-O-(4-nitrobenzyl)-11-phenylselenoimino-papulacandin B in 50 ml of chloroform and the solution is treated at room temperature for 5 minutes with a current of hydrogen sulphide until it becomes almost completely colourless. The reaction solution is carefully concentrated to dryness by evaporation in vacuo, and the residue is applied to a column of 250 g of silica gel and eluted with mixtures of chloroform with increasing proportions (5–20%) of methanol. By concentration by evaporation of appropriate fractions and re-precipitation from acetone/ether, 2.1 g of 11-amino-12-O-(4-nitrobenzyl)-papulacandin B is obtained in the form of a faintly yellow-coloured amorphous powder. UV-spectrum: (ethanol): $\lambda_{max}$ ($\epsilon$): 205 (63800), 239 (48000), 264 (57100);

IR-spectrum: (KBr): 3500, 2950, 2900, 1710, 1615, 1525, 1460, 1345, 1310, 1265, 1175, 1150, 1065, 1040, 1005 $cm^{-1}$.

EXAMPLE 3

12-O-Methyl-11-phenylselenoimino-papulacandin B

There are added to a solution of 5 g of papulacandin B-12-methyl ether in 80 ml of tetrahydrofuran at room temperature, while stirring, 4 g of hexamethyldisilazane and, after 5 minutes, 4.8 g of phenylselenic acid anhydride, the solution immediately changing to a deep red colour. The reaction solution is stirred at room temperature for a further 7 minutes, poured onto ice water and extracted three times with ethyl acetate. The combined organic phases are washed twice with water, dried over sodium sulphate and concentrated to dryness by evaporation. The residue is applied to a column of 200 g of silica gel and eluted with mixtures of chloroform with increasing proportions (2–10%) of methanol. By concentration by evaporation of appropriate fractions, 2.0 g of 12-O-methyl-11-phenylselenoimino-papulacandin B are obtained in the form of a deep red amorphous powder.

EXAMPLE 4

11-Amino-12-O-methyl-papulacandin B 2.3 ml of triethylamine are added to a solution of 2 g of 12-O-methyl-11-phenylselenoimino-papulacandin B in 100 ml of chloroform. Then, while stirring at room temperature, a current of hydrogen sulphide is introduced for a period of 10 minutes until the previously deep red solution substantially loses its colour. The reaction solution is carefully concentrated to dryness by evaporation in vacuo and the evaporation residue is chromatographed on a column of 120 g of silica gel. By elution with chloroform with increasing proportions (5–20%) of methanol and concentration by evaporation of the appropriate fractions, a crude product is obtained which, after precipitation from acetone/ether, yields 1 g of 11-amino-12-O-methyl-papulacandin B in the form of a faintly yellow-coloured amorphous powder. UV-spectrum (ethanol): $\lambda_{max}$ ($\epsilon$): 238 (41 200), 265 (37 200), 294 (shoulder); IR-spectrum (KBr): 3500, 2950, 1705, 1620, 1525, 1460, 1385, 1345, 1310, 1265, 1150, 1065 $cm^{-1}$.

EXAMPLE 5

11-Acetylamino-12-O-(4-nitrobenzyl)-papulacandin B 2 ml of acetic acid anhydride are added to a solution of 150 mg of 11-amino-12-O-(4-nitrobenzyl)-papulacandin B in 2 ml of methanol and the solution is left to stand at 0° C. for 2 hours. The solution is carefully concentrated to dryness by evaporation in a high vacuum and the evaporation residue is chromatographed on a preparative silica gel thick layer plate with a mixture of chloroform/methanol (4:1) as eluant. After isolation of the product from the appropriate zone and re-precipitation from acetone/ether, 100 mg of 11-acetylamino-12-O-(4-nitrobenzyl)-papulacandin B are obtained in the form of faintly yellow-coloured amorphous powder. The $^{13}$C-NMR spectrum corresponds to the quoted structure, inter alia by the following maxima (in ppm) C(8): 140.8, C(9): 118.2, C(10): 155.2, C(11): 112.9, C(12): 153.9, C(13): 107.9.

EXAMPLE 6

11-Acetylamino-papulacandin B 220 mg of zinc powder are added to a solution of 110 mg of 11-acetylamino-12-O-(4-nitrobenzyl)-papulacandin B in 4 ml of methanol and 14 ml of acetic acid and the solution is stirred intensively at 0° C. for 20 minutes. The reaction solution is filtered through kieselguhr, the filtrate is concentrated to dryness by evaporation and the evaporation residue is chromatographed on a preparative silica gel thick layer plate with a mixture of chloroform/methanol (4:1) as eluant, resulting in 15 mg of amorphous 11-acetylamino-papulacandin B.

EXAMPLE 7

11-Mesylamino-12-O-(4-nitrobenzyl)-papulacandin B 47 mg of mesyl chloride are added to a solution of 300 mg of 11-amino-12-O-(4-nitrobenzyl)-papulacandin B in 10 ml of tetrahydrofuran with 20 drops of pyridine and the solution is left to stand at room temperature for 15 hours. The reaction solution is poured onto ice water, saturated with sodium chloride and extracted three times with ethyl acetate. The combined organic extracts are washed with water, dried over sodium sulphate and concentrated by evaporation. The residue (340 mg) is chromatographed on preparative silica gel thick layer plates with a mixture of chloroform/methanol (4:1) as eluant. 205 mg of 11-mesylamino-12-O-(4-nitrobenzyl)-papulacandin B are obtained in the form of colourless amorphous powder, the $^{13}$C-NMR spectrum of which, in agreement with the quoted structure, has, inter alia, the following maxima (in ppm): C(8): 143.0, C(9): 118.9, C(10): 157.0, C(11): 111.8, C(12): 154.8, C(13): 101.2, aromat. signals: 149.9, 146.0, 128.9, 124.7.

EXAMPLE 8

11-Mesylamino-papulacandin B 400 mg of zinc powder are added to a solution of 200 mg of 11-mesylamino-12-O-(4-nitrobenzyl)-papulacandin B in 3 ml of methanol and 7 ml of glacial acetic acid and the mixture is shaken intensively at room temperature for 40 minutes and filtered through kieselguhr. The filtrate is carefully concentrated to dryness by evaporation, and the residue is chromatographed on a column of 15 g of silica gel. By elution with mixtures of chloroform with increasing proportions (5–20%) of methanol, fractions are obtained which, after customary processing, yield 80 mg of 11-mesylamino-papulacandin B in the form of faintly yellow-coloured amorphous powder. In agreement with the quoted structure, the product exhibits, inter alia, the following maxima (in ppm) in the $^{13}$C-NMR spectrum: C(8): 142.4, C(9): 117.2, C(10): 156.8, C(11): 110.6, C(12): 153.7, C(13): 103.8.

EXAMPLE 9

12-O-(4-Nitrobenzyl)-11-N'-(4-nitrobenzyloxycarbonyl)-glycylamino-papulacandin B 680 mg of dicyclohexylcarbodiimide, 880 mg of N-(4-nitrobenzyloxycarbonyl)-glycine and 400 mg of N-ethylmorpholine are added in succession to a solution of 1 g of 11-amino-12-O-(4-nitrobenzyl)-papulacandin B in 80 ml of tetrahydrofuran, and the mixture is stirred at room temperature for 3.5 hours. The resulting fine precipitate is filtered off, water is added to the filtrate and the aqueous solution is extracted five times with ethyl acetate. The combined organic phases are washed with water, dried over sodium sulphate and concentrated to dryness by evaporation. The residue is chromatographed over a column of 20 g of silica gel. By elution with mixtures of chloroform with increasing proportions (10–100%) of methanol, there are obtained from fractions with chloroform/methanol (1:1) and with methanol alone, 850 mg of concentrated product which, after a further purification on preparative silica gel thick layer plates (4 plates, 20×100 cm, layer thickness 1.5 mm) with a mixture of chloroform/methanol/acetic acid/water (80:18:1:1) as eluant, yields 425 mg of 12-O-(4-nitrobenzyl)-11-N'-(4-nitrobenzyloxycarbonyl)-glycylamino-papulacandin B in the form of colourless amorphous powder. In agreement with the quoted structure, the product exhibits, inter alia, the following maxima in the $^{13}$C-NMR spectrum (in ppm): (NH-COCH$_2$—) 171.1, (NH-COOCH$_2$) 158.7, C(8): ~140, C(9): 118.2, C(10): 154.0, C(11): 112.3, C(12): 155.6, C(13): 101.8; aromatic signals: 66.4, 124.6, 128.9, 129.1, 146.2, 148.8.

EXAMPLE 10

11-Glycylamino-papulacandin B 640 mg of zinc powder are added to a solution of 320 g of 12-O-(4-nitrobenzyl)-11-N'-(4-nitrobenzyloxycarbonyl)-glycylamino-papulacandin B in 9 ml of methanol and 21 ml of glacial acetic acid, and the mixture is shaken for 30 minutes at room temperature and filtered through kieselguhr. The filtrate is carefully concentrated to dryness by evaporation in a high vacuum and the residue is chromatographed over a column of 120 g of Sephadex ® LH-20. The fractions eluted with methanol yield 285 mg of concentrated product which, after further chromatography over Sephadex ® LH-20, yields 95 mg of 11-glycylamino-papulacandin B in the form of colourless amorphous powder.

EXAMPLE 11

12-O-(4-Nitrobenzyl)-11-(2-oxoimidazolidinecarboxamido)-papulacandin B 204 mg of 2-oxoimidazolidinyl-1-carboxylic acid chloride and 1 ml of pyridine are added to a solution of 1.2 g of 11-amino-12-O-(4-nitrobenzyl)-papulacandin B in 40 ml of tetrahydrofuran and the solution is stirred at 0° C. for 1.5 hours. The reaction solution is diluted with ice water, saturated with sodium chloride and extracted three times with ethyl acetate. The combined organic extracts are washed with water, dried over sodium sulphate and concentrated to dryness by evaporation. The residue is chromatographed over a column of 100 g of silica gel. By elution with increasing proportions (10-20%) of methanol fractions are obtained which, after concentration by evaporation, yield 875 mg of 12-O-(4-nitrobenzyl)-11-(2-oxoimidazolidinecarboxamido)-papulacandin B in the form of faintly yellow-coloured amorphous powder. In agreement with the quoted structure, the $^{13}$C-NMR spectrum has, inter alia, the following maxima (in ppm): C(8): 140.0, C(9): 118.4, C(10): 154.3, C(11): 112.9, C(12): 153.7, C(13): 101.9; aromatic signals: 148.7, 146.2, 128.9, 124.6.

EXAMPLE 12

11-(2-Oxoimidazolidinecarboxamido)-papulacandin B 1760 mg of zinc powder are added to a solution of 875 mg of 12-O-(4-nitrobenzyl)-11-(2-oxoimidazolidine)-carboxamido-papulacandin B in 12 ml of methanol and 30 ml of glacial acetic acid and the mixture is shaken intensively for 45 minutes at room temperature and filtered through kieselguhr. The filtrate is carefully concentrated to dryness by evaporation in a high vacuum and the residue is chromatographed over a column of 100 g of silica gel. By elution with mixtures of chloroform with increasing proportions (10-20%) of methanol fractions are obtained which, on concentration by evaporation, yield 450 mg of 11-(2-oxoimidazolidinecarboxamido)-papulacandin B in the form of colourless amorphous powder. In agreement with the quoted structure the $^{13}$C-NMR spectrum has, inter alia, the following maxima (in ppm): C(8): 140.3, C(9): 116.7, C(10): 154.7, C(11): 111.6, C(12): 153.9, C(13): 104.3, —N-H—CO—N<152.1, 160.2.

EXAMPLE 13

12-O-(4-Nitrobenzyl)-11-[L-2-(4-nitrobenzyloxycarbonyl)-1-(4-nitrobenzyloxycarbonylamino)-ethoxycarbonylamino]papulacandin B 45 mg of O-chloroformyl-N-(4-nitrobenzyloxycarbonyl)-L-serine-4-nitrobenzyl ester are added to a solution of 100 mg of 12-O-(4-nitrobenzyl)-papulacandin B in 5 ml of tetrahydrofuran with 10 drops of pyridine and the solution is stirred for 45 minutes at 0° C. The reaction solution is poured onto ice water, saturated with sodium chloride and extracted three times with ethyl acetate. The combined organic extracts are washed with water, dried over sodium sulphate and concentrated by evaporation in vacuo. The residue is chromtographed on a preparative silica gel thick layer plate with a mixture of chloroform/methanol (4:1) as eluant. There is obtained 137 mg of the title compound (formula I,

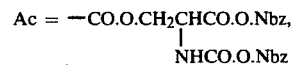

R=Nbz; Nbz=4-nitrobenzyl).

EXAMPLE 14

12-O-Methyl-11-[L-2-(4-nitrobenzyloxycarbonyl)-1-(4-nitrobenzyloxycarbonylamino)-ethoxycarbonylamino]-papulacandin B 360 mg of O-chloroformyl-N-(4-nitrobenzyloxycarbonyl)-L-serine-4-nitrobenzyl ester and 0.3 ml of pyridine are added to a solution of 770 mg of 11-amino-12-O-methyl-papulacandin B in 25 ml of tetrahydrofuran and the solution is stirred for 45 minutes at +5° C. Ice water is added to the reaction solution, this is saturated with sodium chloride and extracted five times with ethyl acetate. The combined organic extracts are washed with water, dried over sodium sulphate and concentrated to dryness by evaporation. The residue is chromatographed over a column of 20 g of silica gel. By elution with mixtures of chloroform with an increasing proportion (5-20%) of methanol fractions are obtained which, after concentration by evaporation, yield 700 mg of the title compound in the form of faintly yellow-coloured amorphous powder (formula I

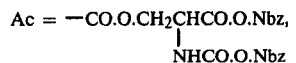

R=CH$_3$; Nbz=4-nitrobenzyl).

EXAMPLE 15

12-O-Methyl-11-(3-O-serinyl)-carbonylamino-papulacandin B 1.4 g of zinc powder are added to a solution of 700 mg of 12-O-methyl-11-[L-2-(4-nitrobenzyloxycarbonyl)-1-

(4-nitrobenzyloxycarbonylamino)-ethoxycarbonylamino]-papulacandin B (produced in accordance with Example 14) in 9 ml of methanol and 21 ml of acetic acid and the solution is shaken at room temperature for 45 minutes and filtered through kieselguhr. The filtrate is carefully concentrated to dryness by evaporation in a high vacuum and the residue is chromatographed over a column of 70 g of silica gel UPC-12 ® (reversed phase) with aqueous acetonitrile as eluant. 525 mg of concentrated material are obtained, which is further resolved on 5 preparative silica gel thick layer plates, a mixture of n-butanol/acetic acid/water (11:3:7) being used as eluant. The main zone (580 mg) is chromatographed again on a column of 100 g of Sephadex ® LH-20, yielding 80 mg of the title compound [formula I, Ac=—CO.O.CH$_2$CH(NH$_2$)COOH-(—L—); R=CH$_3$] in the form of colourless amorphous powder.

EXAMPLE 16

11-Acetylamino-12-O-methyl-papulacandin B

A mixture of 450 mg of 11-amino-12-O-methyl-papulacandin B, 2 ml of methanol and 1 ml of acetic acid anhydride is stirred for 30 minutes at 0° C., and carefully concentrated to dryness by evaporation. The residue is chromatographed on a preparative silica gel thick layer plate with chloroform/methanol (4:1). 70 mg of 11-acetylamino-12-O-methyl-papulacandin B are obtained, the $^{13}$C-NMR spectrum of which has, inter alia, the following maxima (in ppm): C(8): 141.0, C(9): 117.7, C(10): 155.7, C(11): 112.4, C(12): 146.7, C(13): 100.5, —COCH$_3$: 172.5, —COCH$_3$: 22.6.

EXAMPLE 17

12-O-Methyl-11-[N'-(4-nitrobenzyloxycarbonyl)-glycylamino]-papulacandin B 34 mg of dicyclohexylcarbodiimide, 44 mg of N-(4-nitrobenzyloxycarbonyl)-glycine and 20 ml of N-ethylmorpholine are added in succession to a solution of 52 mg of 11-amino-12-O-methyl-papulacandin B in 4 ml of tetrahydrofuran. The reaction solution is stirred at room temperature for 3 hours and filtered. Water is added to the filtrate and the aqueous phase is extracted five times with ethyl acetate. The organic extracts are concentrated to dryness by evaporation and chromatographed on a preparative silica gel thick layer plate, chloroform/methanol (4:1) being used as eluant. 40 mg of 12-O-methyl-11-[N'-(4-nitrobenzyloxycarbonyl)-glycylamino]-papulacandin B are obtained.

EXAMPLE 18

11-Glycylamino-12-O-methyl-papulacandin B 80 mg of zinc powder are added to a solution of 40 mg of 12-O-methyl-11-[N'-(4-nitrobenzyloxycarbonyl)-glycylamino]-papulacandin B in 1 ml of methanol and 3 ml of acetic acid and the mixture is shaken for 30 minutes at room temperature and filtered through kieselguhr. The filtrate is carefully concentrated to dryness by evaporation in a high vacuum and chromatographed on a silica gel thick layer plate with n-butanol/glacial acetic acid/water (11:3:7) as eluant. 22 ml of 11-glycylamino-12-O-methyl-papulacandin B are obtained.

EXAMPLE 19

A pharmaceutical preparation in the form of a gel for the treatment of mycoses containing 11-(2-oxoimidazolidinecarboxamido)-papulacandin B (referred to hereinafter as active ingredient).

Gel containing 0.05% of active ingredient

To produce 5 liters of gel, 100 g of highly viscous methylcellulose is mixed with 500 g of propyleneglycol and 3.25 ml of *Aqua conservans* and the mixture is allowed to swell out to a homogeneous mucilage. Then, a suspension of 2.5 g of active ingredient in 1 liter of *Aqua conservans* is admixed. Finally, the mixture is made up to 5 liters with *Aqua conservans* and carefully mixed and the resulting gel is filled into tubes.

There is to be understood by *Aqua conservans* an aqueous solution of 0.07% of p-hydroxybenzoic acid methyl ester (methylparabene) and 0.03% of p-hydroxybenzoic acid propyl ester (propylparabene).

EXAMPLE 20

A pharmaceutical preparation for the treatment of fungal infections containing 11-(2-oxoimidazolidinecarboxamido)-papulacandin B.

Gels containing 0.5–1% of the active ingredient are produced in the manner described in Example 19 using the necessary quantity of the same papulacandin B active ingredient.

I claim:

1. An N-acylated 11-amino derivative of papulacandin A or B of the formula I

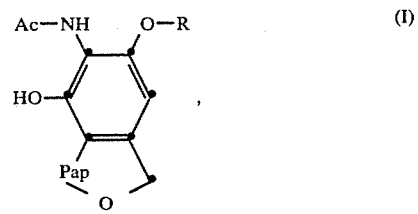

in which Pap is the remainder of papulacandin A or B, R represents methyl or hydrogen and Ac represents the acyl radical of an α-amino acid which occurs naturally as a peptide-building unit, or of a lower alkanesulfonic acid having a maximum of 7 carbon atoms, or a lower alkanoic acid having a maximum of 7 carbon atoms, or the acyl radical Ac$_t$ of the formula

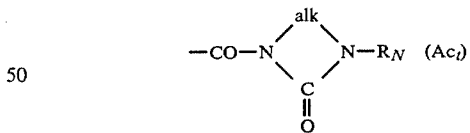

in which R$_N$ represents hydrogen, formyl, lower alkoxycarbonyl, carbamoyl, hydroxy-lower alkyl or a hydrocarbyl having a maximum of 8 carbon atoms, and alk represents an alkylene radical having from 2–8 carbon atoms which separates the two nitrogen atoms from each other by a minimum of 2 and a maximum of 4 carbon atoms, or an acid addition salt of said compound in which Ac is the acyl radical of an α-amino acid.

2. A compound according to claim 1, in which in the formula I Pap is Pap$_B$, R represents hydrogen and Ac represents the acyl radical of an α-amino acid which occurs naturally as a peptide-building unit; or an acid addition salt thereof.

3. A compound according to claim 2, which is 11-glycylamino-papulacandin B.

4. A compound according to claim 1, in which in the formula I Pap is Pap$_B$, R represents hydrogen or methyl and Ac represents a lower alkanoyl radical having a maximum of 7 carbon atoms.

5. A compound according to claim 4, which is 11-acetamino-12-O-methyl-papulacandin B.

6. A compound according to claim 1, in which in the formula I Pap is Pap$_B$, R represents hydrogen and Ac represents the acyl radical of a lower alkanesulphonic acid having a maximum of 7 carbon atoms.

7. A compound according to claim 6, which is 11-mesylamino-papulacandin B.

8. A compound according to claim 1, in which in the formula I Pap is Pap$_B$, R represents hydrogen or methyl and Ac represents the acyl radical Ac$_t$ of the formula

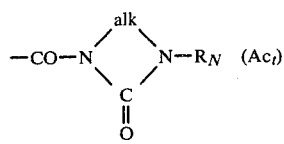 (Ac$_t$)

in which R$_N$ represents hydrogen, formyl, lower alkoxycarbonyl, carbamoyl, hydroxy-lower alkyl or a hydrocarbyl having a maximum of 8 carbon atoms, and alk represents an alkylene radical having from 2-8 carbon atoms which separates the two nitrogen atoms from each other by a minimum of 2, and a maximum of 4, carbon atoms.

9. A compound according to claim 8, in which in the acyl radical Ac$_t$ alk represents ethylene and R$_N$ represents hydrogen, methyl or benzyl.

10. A compound according to claim 8, which is 11-(2-oxoimidazolidinecarboxamido)-papulacandin B.

11. 12-O-methyl-11-(3-O-L-seryl)-carbonylamino-papulacandin B.

12. Process for the manufacture of 11-aminopapulacandin derivatives of the formula II

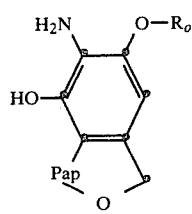 (II)

in which Pap is the remainder of papulacandin A or B and R$_o$ represents methyl or a hydroxy-protecting group Y, and their acid addition salts, characterised in that a papulacandin derivative of the formula IV

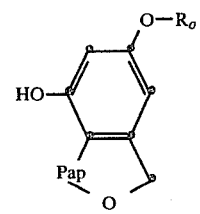 (IV)

in which Pap and R$_o$ have the meanings given above is (a) reacted with an arylselenic acid anhydride and hexa-lower alkyldisilazane and subsequently (b) treated with hydrogen sulfide or a thiol.

13. An 11-aminopapulacandin derivative of the formula II

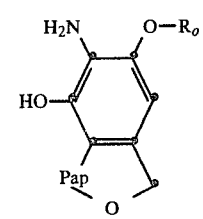 (II)

in which Pap is the remainder of papulacandin A or B and R$_o$ represents methyl, and an acid addition salt thereof.

14. A compound according to claim 13, in which in the formula II R$_o$ represents methyl.

15. A compound according to claim 13, which is 11-amino-12-O-methyl-papulacandin B.

16. A pharmaceutical preparation for use as antibiotic containing an effective amount of a compound according to any one of claims 1, 11, or 13 together with a pharmaceutical carrier.

17. Therapeutic method for inhibiting or eliminating microbial infections in a warm-blooded animal by the administration to this warm-blooded animal of a compound according to any one of claims 1, 12, or 13 alone or in the form of a pharmaceutical preparation in amounts that are effective for the inhibition or elimination of the infection in this warm-blooded animal.

18. Method according to claim 17, characterised in that the compound or preparation is administered to a human.

* * * * *